United States Patent [19]

Fukushige et al.

[11] Patent Number: 5,334,749

[45] Date of Patent: Aug. 2, 1994

[54] POLYMERIZABLE PHENOL COMPOUND

[75] Inventors: Yuuichi Fukushige; Ken Iwakura; Masato Satomura, all of Shizuoka, Japan

[73] Assignee: Fuji Photo Film Co., Ltd., Kanagawa, Japan

[21] Appl. No.: 992,540

[22] Filed: Dec. 17, 1992

[30] Foreign Application Priority Data

Dec. 18, 1991 [JP] Japan .................. 3-333774

[51] Int. Cl.⁵ .............................. C07C 69/88
[52] U.S. Cl. ........................ 560/67; 560/221
[58] Field of Search ................. 560/67, 221

[56] References Cited

U.S. PATENT DOCUMENTS 5,019,280  5/1991  Caswell et al. .............. 252/8.8

FOREIGN PATENT DOCUMENTS

| | | |
|---|---|---|
| 2048176 | 1/1972 | Fed. Rep. of Germany . |
| 59-83693 | 5/1984 | Japan . |
| 60-141587 | 7/1985 | Japan . |
| 62-99190 | 5/1987 | Japan . |
| 63173682 | 7/1988 | Japan . |
| 4226944 | 8/1992 | Japan . |

Primary Examiner—Paul J. Killos

Attorney, Agent, or Firm—Sughrue, Mion, Zinn, Macpeak & Seas

[57] ABSTRACT

A polymerizable phenol compound represented by the formula (I):

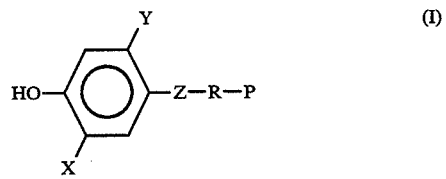

wherein X represents a hydrogen atom, an alkyl group, a halogen atom, an alkylsulfonyl group, a hydroxyl group or a substituted or unsubstituted phenyl group; Y represents a hydrogen atom, a hydroxyl group, an alkoxy-carbonyl group, a halogen atom, an alkyl group, an alkyl-sulfonyl group, an alkoxy group, an alkanoyloxy group, an acryloyloxy group or a methacryloyloxy group; Z represents —COO—, —O—, —SO$_2$— or —SO$_2$NH—; R represents a divalent linkage group having an —O—, —S—, —SO$_2$—, —CO—, —NH—, or a cyclic structure; and P represents an acryloyloxy group or a methacryloyloxy group.

4 Claims, No Drawings

POLYMERIZABLE PHENOL COMPOUND

FIELD OF THE INVENTION

The present invention relates to a polymerizable phenol compound which is useful as a polymerizable monomer in recording materials.

BACKGROUND OF THE INVENTION

Various polymerizable phenol compounds are known to be useful compounds for recording materials and described in JP-A-63-173682, JP-A-59-83693, JP-A-60-141587, JPA-62-99190, Japanese Patent Application Nos. Hei-2-150319 and Hei-2-156381 and U.S. Pat. No. 5,091,280; however, the compounds described in the above known references do not include polymerizable phenol compounds which have an —O—, —S—, —SO$_2$—, —CO—, —NH— or cyclic structure in a linkage group therein.

SUMMARY OF THE INVENTION

An object of the present invention is to provide a novel polymerizable phenol compound having polymerization sensitivity, preservability, improved suitability for emulsification or improved solubility, and being useful for applications such as developers for colorless dyes, raw materials for polymers, raw materials for polyfunctional monomers, or other materials for various uses, for example, heat-sensitive paper, pressure-sensitive paper, transparent heat-sensitive uses or light- and heat-sensitive uses.

Other objects of the present invention will be apparent from the following description.

The above-described objects of the present invention can be achieved by a polymerizable phenol compound represented by the following formula (i):

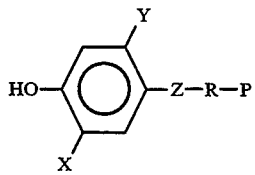

(I)

wherein X represents a hydrogen atom, an alkyl group, a halogen atom, an alkylsulfonyl group, a hydroxyl group or a substituted or unsubstituted phenyl group; Y represents a hydrogen atom, a hydroxyl group, an alkoxycarbonyl group, a halogen atom, an alkyl group, an alkylsulfonyl group, an alkoxy group, an alkanoyloxy group, an acryloyloxy group or a methacryloyloxy group; Z represents —COO—, —O—, —SO$_2$— or —SO$_2$NH—; R represents a divalent linkage group having an —O—, —S—, —SO$_2$—, —CO—, —NH—, or a cyclic structure; and P represents an acryloyloxy group or a methacryloyloxy group.

DETAILED DESCRIPTION OF THE INVENTION

Preferred examples of groups in formula (I) are as follows. X in formula (I) preferably represents a hydrogen atom, a halogen atom, an alkyl group having 1 to 3 carbon atoms or a substituted or unsubstituted phenyl group, with the hydrogen atom or a chlorine atom being particularly preferred. Y in formula (I) preferably represents a hydrogen atom, a hydroxyl group, an alkoxycarbonyl group, an alkanoyloxy group, with the hydrogen atom or the hydroxyl group being particularly preferred. Z preferably represents —COO— or —SO$_2$—. R in formula (I) preferably represents one of the following structures.

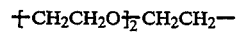

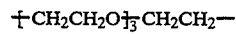

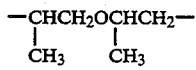

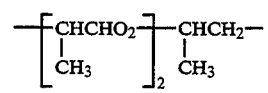

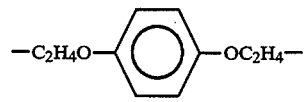

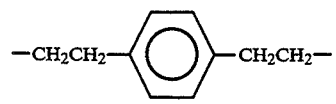

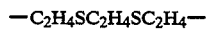

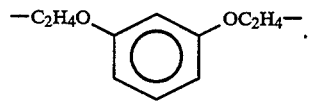

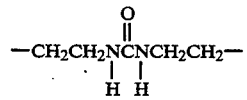

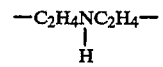

Of the above structures particularly preferred are those having an oxygen atom in the linkage group.

Specific examples of the polymerizable phenol compounds of the present invention are shown below.

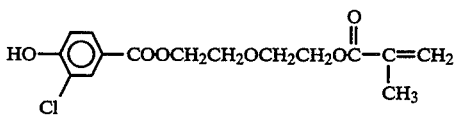

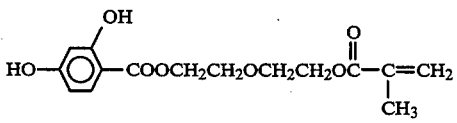

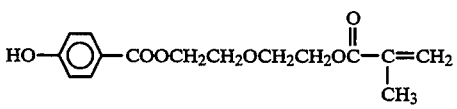

-continued

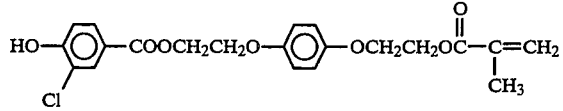
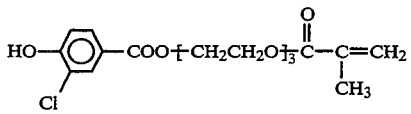
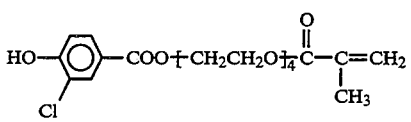
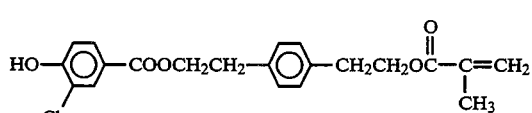
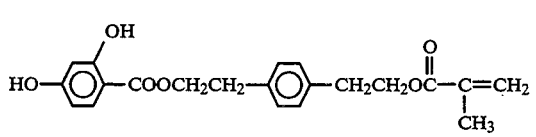
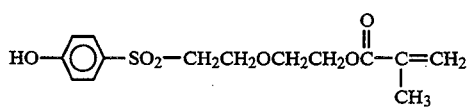
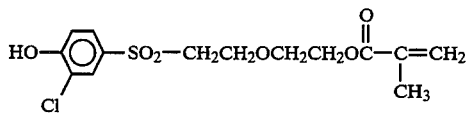
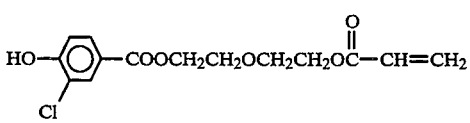
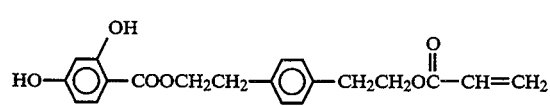
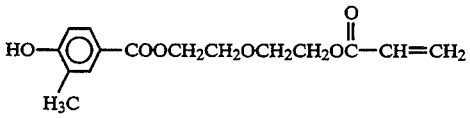
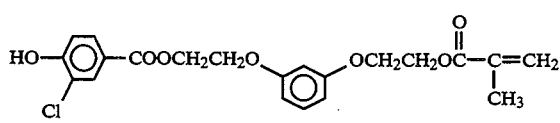
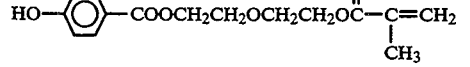

-continued

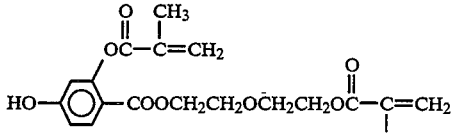
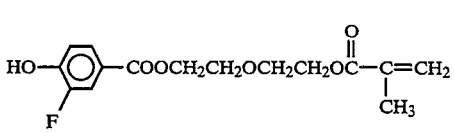
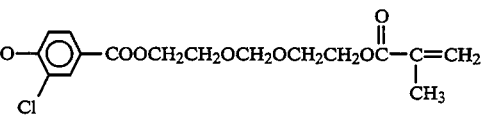
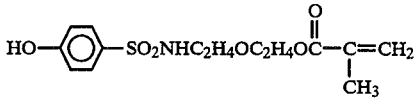

The compounds of the present invention can be produced by acryloylating or methacryloylating the corresponding phenol compounds having an alcoholic hydroxyl group. This method is a selective esterification method, in which a phenol compound having an alcoholic hydroxyl group is reacted with an acid chloride in an organic solvent together with an amide or urea compound. Details of this selective esterification method are described in JP-A-4-149155.

The corresponding phenol compounds having an alcoholic hydroxyl group can be synthesized by various method and, most usually, by reacting a benzoic acid ester, preferably methyl benzoate, with a diol compound in the presence of a catalyst or by reacting the corresponding benzoic acid compound with a haloalcohol.

The polymerizable phenol compounds of the present invention are used as electron-accepting compounds in general pressure-sensitive recording materials and heat-sensitive recording materials and also as electron-accepting compounds in light-sensitive, heat-sensitive recording materials described, for example, in U.S. Pat. No. 5,091,280 and JP-A-2-156381.

The present invention is described with reference to the following examples but should not be construed as being limited thereto. In the examples, percentages by weight are used unless otherwise indicated.

EXAMPLE 1

A 500-ml eggplant type flask was charged with 50 g of 3-chloro-4-hydroxybenzoic acid methyl ester, 285 g of diethyleneglycol and further with 2.5 g of PTS (p-toluenesulfonic acid monohydrate) as a catalyst to form a mixture. The mixture was heated with stirring on an oil bath, externally regulated at a temperature of 150° C., to react the mixture for 5 hours. Thereafter, excess diethylene glycol therein was removed by means of vacuum distillation. The residue therein was poured into ice water and the precipitated crystals were recrystallized using benzene/ethanol to obtain 49 g of 3-chloro-4-hydroxybenzoic acid [2-(2-hydroxyethoxy)ethyl]-ester (melting point: 77.5° to 78° C.). To 100 ml of an acetonitrile solution containing 30 g of the 3-chloro-4-hydroxybenzoic acid [2-(2-hydroxyethoxy)ethyl]-ester, 57.2 g of N-methylpyrrolidone and further 36 g of methacrylic acid chloride were added with stirring to form a solution. The solution was stirred for 8 hours at 40° C. to react the solution. Thereafter, excess methacrylic acid chloride was removed by means of vacuum distillation. The reaction mixture remaining therein was poured into ice water, and the precipitated crystals were obtained by filtration. The crystals were recrystallized with ethyl acetate/n-hexane to obtain 3-chloro-4-hydroxybenzoic acid [2-(2-methacryloyloxyethoxy)ethyl]ester (melting point: 57° to 58.5° C.).

EXAMPLE 2

A 300-ml eggplant type flask was charged with 16.3 g of 3-chloro-4-hydroxybenzoic acid methyl ester, 87 g of 1,4-(2-hydroxyethoxy)benzene and further with 0.8 g of PTD (p-toluenesulfonic acid monohydrate) as a catalyst to form a mixture. The mixture was stirred with heating on an oil bath, externally regulated at a temperature of 150° C., to react the mixture for 5 hours. The reaction mixture was poured into ice water followed by extracting with ethyl acetate, drying over anhydrous magnesium sulfate, concentrating and separating with a column using ethylacetate/n-hexane to obtain 29 g of 3-chloro-4-hydroxybenzoic acid 2-[4-(β-hydroxyethoxy)-phenoxy]ethyl ester (melting point: 87° to 88° C.). To 50 ml of an acetonitrile solution containing 10 g of the 3-chloro-4-hydroxybenzoic acid 2-[4-(β-hydroxyethoxy)-phenoxy]ethyl ester, 13.9 g of N-methylpyrrolidone and further 8.78 g of methacrylic acid chloride were added with stirring to form a solution. The solution was stirred at 40° C. for 8 hours to react the solution. Thereafter, excess methacrylic acid chloride was removed by means of vacuum distillation. The reaction mixture remaining therein was poured into ice water and the precipitated crystals were obtained by filtration. The crystals were recrystallized with ethylacetate/n-hexane to obtain 3-chloro-4-hydroxybenzoic acid 2-[4-(β-methacryloyloxyethoxy)phenoxy]ethyl ester (melting point: 105° to 106° C.).

While the invention has been described in detail and with reference to specific embodiments thereof, it will be apparent to one skilled in the art that various changes and modifications can be made therein without departing from the spirit and scope thereof.

What is claimed is:

1. A polymerizable phenol compound represented by formula (I):

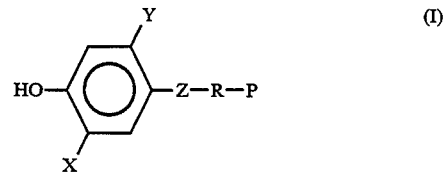

wherein X represents a hydrogen atom or a chlorine atom; Y represents a hydrogen atom; Z represents —COO—, —O—, —SO$_2$— or —SO$_2$NH—; R represents an alkylene group having an —O—, —S—, —SO$_2$—, —CO—, —NH— or a phenylene group; and P represents an acryloyloxy group or a methacryloyloxy group.

2. A polymerizable phenol compound as in claim 1, wherein Z represents —COO— or —SO$_2$—.

3. A polymerizable phenol compound as in claim 1, wherein Z represents —COO—.

4. A polymerizable phenol compound as in claim 1, wherein R represents an alkylene group having an oxygen atom.

* * * * *